US010338050B2

(12) United States Patent
Enquist

(10) Patent No.: US 10,338,050 B2
(45) Date of Patent: Jul. 2, 2019

(54) METHOD AND DEVICE FOR DISCRIMINATION BETWEEN NATURAL GAS AND SWAMP GAS

(71) Applicant: INFICON GmbH, Bad Ragaz (CH)

(72) Inventor: Fredrik Enquist, Linköping (SE)

(73) Assignee: INFICON GmbH, Bad Ragaz (CH)

( * ) Notice: Subject to any disclaimer, the term of this patent is extended or adjusted under 35 U.S.C. 154(b) by 0 days.

(21) Appl. No.: 15/329,292

(22) PCT Filed: Jul. 20, 2015

(86) PCT No.: PCT/EP2015/066555
§ 371 (c)(1),
(2) Date: Jan. 26, 2017

(87) PCT Pub. No.: WO2016/016036
PCT Pub. Date: Feb. 4, 2016

(65) Prior Publication Data
US 2017/0227513 A1    Aug. 10, 2017

(30) Foreign Application Priority Data

Jul. 29, 2014    (EP) .................................... 14178963

(51) Int. Cl.
*G01N 33/22*    (2006.01)
*G01N 33/00*    (2006.01)
*G01M 3/02*    (2006.01)

(52) U.S. Cl.
CPC ............ *G01N 33/225* (2013.01); *G01M 3/02* (2013.01); *G01N 33/005* (2013.01)

(58) Field of Classification Search
None
See application file for complete search history.

(56) References Cited

U.S. PATENT DOCUMENTS

| 4,507,558 A * | 3/1985 | Bonne ................ G01N 21/3504 |
| | | 250/338.1 |
| 4,507,588 A | 3/1985 | Asmussen et al. |
| 4,618,855 A | 10/1986 | Harding et al. |
| 4,958,076 A * | 9/1990 | Bonne ................ G01N 21/3504 |
| | | 250/339.13 |
| 2004/0088113 A1 | 5/2004 | Spoonhower et al. |
| 2008/0179199 A1* | 7/2008 | Coignet ............. G01N 27/4074 |
| | | 205/793 |
| 2015/0007638 A1* | 1/2015 | Rella .................. G01N 33/0009 |
| | | 73/40 |

FOREIGN PATENT DOCUMENTS

| JP | 187231 U | 6/1989 |
| JP | 5322688 A | 12/1993 |
| JP | 1123403 A | 1/1999 |
| JP | 2004150636 A | 5/2004 |

* cited by examiner

*Primary Examiner* — Paul M. West
*Assistant Examiner* — Mark A Shabman
(74) *Attorney, Agent, or Firm* — The Webb Law Firm

(57) ABSTRACT

Method for determining whether a gas sample originates from biological processes or from a gas installation being tested and containing a utility gas is characterized in that an increased concentration of hydrogen in the sample as compared to that present in the utility gas is used as evidence that the sample originates from biological decay processes and not from the gas installation under test.

9 Claims, 1 Drawing Sheet

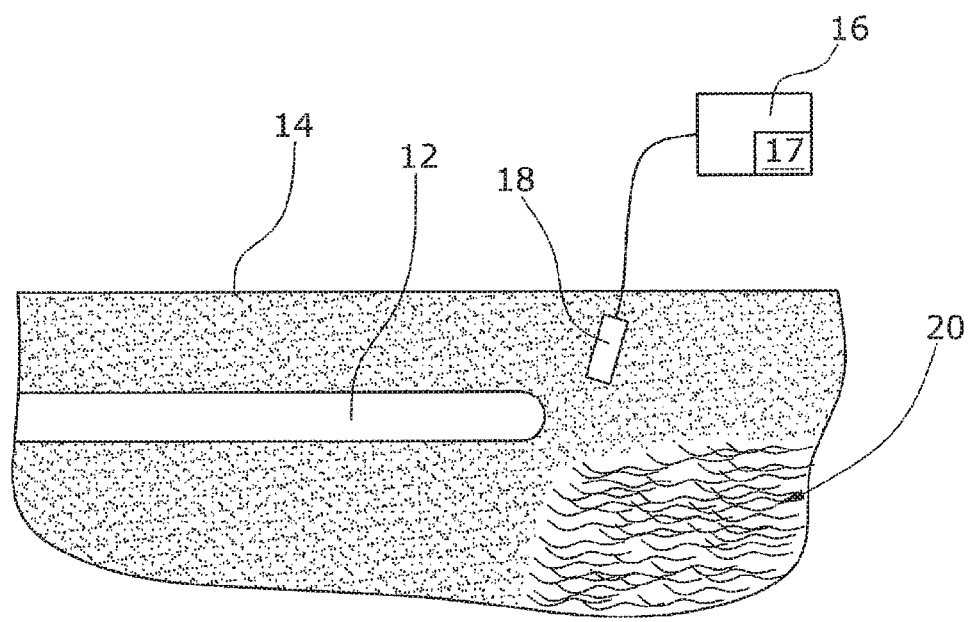

METHOD AND DEVICE FOR DISCRIMINATION BETWEEN NATURAL GAS AND SWAMP GAS

CROSS-REFERENCE TO RELATED APPLICATIONS

This application is the United States national phase of International Application No. PCT/EP2015/066555 filed Jul. 20, 2015, and claims priority to European Patent Application No. 14178963.6 filed Jul. 29, 2014, the disclosures of which are hereby incorporated in their entirety by reference.

FIELD OF THE INVENTION

The present invention relates to a method for very fast determination of whether the origin of registered gas signals is swamp gas or utility gas when searching for leaks in underground utility gas pipes.

BACKGROUND OF THE INVENTION

Regulations throughout the world require regular survey of gas networks to check for unknown leakage. The reason for this is primarily to protect the public from fires and explosions resulting from gas collecting in buildings and other confined spaces. The leak survey is typically carried out by moving a detector, sensitive to one of the main components of the gas, over the surface of the ground above the pipe carrying the gas.

For compressed natural gas (CNG) the main component is typically methane while Liquefied Petroleum Gas (LPG) contains mainly Butane and Propane. In addition to these two more common gas types there is a growing production of biogas even though the pipe network is still very limited. Bio-gas contains mainly methane. All such flammable gases distributed in pipelines or vessels are denoted utility gas in the following.

A fourth type of flammable gas used in some parts of the world is called coal gas or manufactured gas (MG). This contains high levels of hydrogen and is excluded from above the definition of utility gas.

If a utility gas signal is registered it can originate from two main sources; the gas installation under inspection or from biological decay processes. Examples of such biological sources are covered waste dumps, decomposing sewage, landfills etc. Gas originating from such sources is known by numerous names including marsh gas, soil gas, landfill gas and sewer gas. In the following the term swamp gas is used as a common denominator for flammable gas sources of biological origin. In order to avoid unnecessary excavations on swamp gas signals it is desirable to be able to distinguish between real gas leaks from the pipe under survey and indications from swamp gas.

The most common method used to discriminating between utility gas and swamp gas is making an analysis of the components of the gas to determine the presence of ethane gas and/or heavier hydrocarbons such as propane and butane. Most natural gas sources contain 0.5-8% of ethane while swamp gas does not contain any significant amounts of ethane.

There are at present no commercially available gas sensors with a high enough selectivity between methane and ethane to make such an analysis possible in real time. The analysis is, therefore, typically carried out using a gas chromatograph (GC) separating the different components of the gas sample into pulses exiting the chromatograph column at different times. Due to this time separation of the different components, the analysis is possible even with a non-selective sensor.

The GC can be a lab instrument in which case a gas sample is collected in some type of container that is sent off to a laboratory for analysis. Field operable GCs are also available. These can be dedicated instruments or small GC modules integrated into a pipeline leak surveying instrument. The field GCs and especially those integrated into a leak detector are generally less sensitive than the lab units and sample concentration must be above 1% or at least 0.5% to make a certain detection of ethane in the sample.

This fact often makes it necessary to drill probe holes through the paving to allow a high enough concentration of gas to be collected. This makes the effective test time considerably longer and typically in the order of 30 minutes or more.

Another way of discrimination is to detect the presence odorant either by smelling the gas or by using a specific detector. The "manual" method is simple and low cost but not entirely reliable and detectors for the odorants are typically higher grade GCs associated with similar delay and higher costs than for those used for ethane detection. A better performing GC is needed as the odorant concentration is several orders of magnitude lower than the ethane concentration.

In any case, certain discrimination between swamp gas and utility gas is a slow and not always entirely reliable process and there is a need for a simpler and faster method.

SUMMARY OF THE INVENTION

It is an object of the present invention to provide an improved method for determining the source of a detected gas signal, during the routine process of leak surveying buried utility gas pipe lines.

The main difficulty with the ethane analysis method is the lack of affordable and selective sensors that can independently measure methane and ethane. Looking at the composition of the two gas mixtures to distinguish between, it can be seen that there is at least one other component that is different: hydrogen.

Investigating the reported content of utility gases there are seldom any quoted hydrogen levels. It, therefore, seems the amount of hydrogen is insignificant. In swamp gas, on the other hand, there is typically a significant amount of hydrogen. A large number of different microorganisms produce hydrogen under anaerobic conditions and hydrogen is therefore normally found in swamp gas. Reported hydrogen concentration levels are from a few hundred parts per million and up to 1 or 2%.

This invention solves the above described limitations of ethane testing by using a highly sensitive and hydrogen selective gas detector. For this procedure to work properly it is necessary that the detector is several orders of magnitude more sensitive for hydrogen than for any of the gases present in the natural gas, mainly combustible gases but also $CO_2$. It is also necessary that the detector does not react to decreased oxygen content (which is not uncommon for combustible gas sensors).

The absence of hydrogen in the natural gas can easily be confirmed by testing the natural gas with the hydrogen selective sensor.

Detectors with the desired quality are manufactured and sold by INFICON AB in Sweden. The selectivity of these detectors for hydrogen as compared to methane is more than 5 orders of magnitude.

In other words, the invention is based on the principle that the gas sample which is taken during a leakage test of a gas installation is additionally used in order to determine, whether the sample originates from the utility gas within the gas installation or from gas which originates from biological decay processes. The hydrogen content of the utility gas should be determined if not previously known. If the hydrogen content in the detected gas is significantly higher, the sample originates from biological decay processes. The method of the invention can thus be described as including the following steps:

obtaining a gas sample from below the ground surface,
testing the gas sample for the presence of hydrogen,
comparing the hydrogen level within the gas sample with the known hydrogen level of the utility gas within the gas installation to be tested,
deciding that the gas sample originates from biological decay processes, if the hydrogen concentration is above the hydrogen concentration of the utility gas.

Alternative and simpler indicators for a gas sample originating from biological decay processes is that the hydrogen concentration is above than 5 parts per million (ppm) or above 100 ppm.

BRIEF DESCRIPTION OF THE DRAWING

FIG. 1 is a side view of an embodiment of the invention.

DETAILED DESCRIPTION OF THE INVENTION

A gas pipeline 12 is part of a gas installation below the ground surface 14. The tightness of the gas pipeline 12 is to be tested with a leak detector 16. A measurement probe 18 of the leak detector 16 is positioned on the ground surface 14 or into a drilled hole below the ground surface 14 in a region where the gas pipeline 12 and a possible leakage is assumed. A swamp gas producing area 20 is below the ground surface 14 in proximity to the testing probe 18. Therefore, the probe 18 samples either gas leaking from the pipeline 12 or gas originating from biological decay processes within the swamp gas producing area 20.

The gas analyser 16 detects gas within the gas sample. The utility gas within the gas installation contains methane and/or heavier hydrocarbons while the gas originating from the biological decay process (swamp gas) contains mainly methane. In any case this will be picked up by the sensing mechanism of the detector.

In order to determine whether the sample originates from the utility gas installation (gas pipeline 12) or from the swamp gas producing area 20 (gas originating from biological decay processes), the hydrogen content of the gas sample is determined with the leak detector 16. The leak detector includes a hydrogen selective sensor 17 and is therefore sensitive to hydrogen. It is detected whether the hydrogen content is above a certain threshold. The threshold may be based on the previously known hydrogen concentration within the utility gas. The threshold may alternatively be for example 5 ppm or 100 ppm or even larger, depending on the composition of the utility gas and the type of biological decay processes that are assumed in the facility of the gas installation.

The invention claimed is:

1. A method for determining whether a gas sample originates from biological processes or from a gas installation being tested and containing a utility gas containing at least one of methane and heavier hydrocarbons,
   the method comprising the steps of:
   detecting a methane concentration within the gas sample with a field-operable pipeline leak survey gas detector,
   detecting a concentration of hydrogen in the gas sample with a hydrogen selective gas sensor;
   comparing the detected concentration of hydrogen in the gas sample to a concentration of hydrogen present in the utility gas;
   wherein the comparison is used to determine that the gas sample originates from biological decay processes and not from the gas installation being tested if the detected hydrogen concentration is above the hydrogen concentration of the utility gas.

2. The method according to claim 1, further comprising determining whether the concentration of hydrogen in the utility gas contained in the gas installation is below a predetermined level using a hydrogen selective gas sensor before evaluating the hydrogen content in the gas sample.

3. The method of claim 1, wherein the hydrogen comparison is performed simultaneously with a gas leak survey, while the gas installation is being tested.

4. The method according to claim 1, wherein a hydrogen content above 5 ppm in the gas sample is used as evidence that the gas sample originates from biological decay processes.

5. The method according to claim 1, wherein a hydrogen concentration of at least 100 ppm in the gas sample is used as evidence that the gas sample originates from biological decay processes.

6. A device for determining whether a gas sample originates from biological decay processes or from a gas installation being tested and containing a utility gas containing at least one of methane and heavier hydrocarbons, comprising:
   a field operable pipeline leak survey gas detector adapted to detect methane, and
   a hydrogen selective gas sensor integrated in the field operable pipeline leak survey gas detector, wherein said detector can be used for comparing the detected concentration of hydrogen in the gas sample to a concentration of hydrogen present in the utility gas, and to determine that the gas sample originates from biological decay processes and not from the gas installation being tested if the detected hydrogen concentration is above the hydrogen concentration of the utility gas.

7. The device according to claim 6, wherein the hydrogen content in the gas sample is compared with a hydrogen content in the utility gas of the gas installation being tested simultaneously with a gas leak survey, while the gas installation is being tested.

8. The device according to claim 6, wherein a hydrogen content above 5 ppm in the gas sample is used as evidence that the gas sample originates from biological decay processes.

9. The device according to claim 6, wherein a hydrogen concentration of at least 100 ppm in the gas sample is used as evidence that the gas sample originates from biological decay processes.

* * * * *